United States Patent [19]

Johnson

[11] 4,304,139

[45] Dec. 8, 1981

[54] CONTINUOUS SURFACE SOIL SAMPLER

[76] Inventor: Gordon V. Johnson, 2226 Tanglewood Cir., Stillwater, Okla. 74074

[21] Appl. No.: 153,595

[22] Filed: May 27, 1980

[51] Int. Cl.³ .............................................. G01N 1/08
[52] U.S. Cl. .............................. 73/864.32; 73/864.41
[58] Field of Search ................. 73/421 R, 425, 425.2, 73/424

[56] References Cited

U.S. PATENT DOCUMENTS 3,331,249 7/1967 Boxrud .................................. 73/424
3,625,296 12/1971 Mabry ................................ 73/425.2

FOREIGN PATENT DOCUMENTS 581410 11/1977 U.S.S.R. ............................ 73/425.2

Primary Examiner—S. Clement Swisher
Attorney, Agent, or Firm—Head & Johnson

[57] ABSTRACT

A soil sampling device secured to a vehicle for taking soil samples while the vehicle is moving is provided with a housing having a first and second portion. The first portion has a chamber extending outwardly therefrom and the second portion has a soil inlet opening. Soil retaining baffles are disposed within the second portion adjacent the soil inlet opening. The housing is pivotally connected to a mounting bar and brace, which is secured to the vehicle. A hydraulic piston rotates the housing so that the second portion strikes the ground and a small portion of soil is injected into the inlet opening and retained by the soil retaining baffles. The housing is rotated and the captured soil is directed to the chamber whereupon the soil sampler is in position to take another soil sample.

15 Claims, 8 Drawing Figures

CONTINUOUS SURFACE SOIL SAMPLER

BACKGROUND OF THE INVENTION

1. Field of the Invention

The present invention relates to a soil sampling device and, more particularly, to such a device which is adapted to take soil samples and mix each separate soil sample together all while being moved across the field.

2. Description of the Prior Art

With the ever increasing demand for food around the world there is an ever increasing demand on the farmer to produce the most crops from his limited number of acres. Various chemicals and fertilizers have been developed which greatly improve the growth characteristics of plants. These fertilizers can be made so that they add the necessary nutriments to a plant which the soil is lacking and without the addition of other nutriments which the soil may be saturated with. In order to determine the characteristics of the soil to determine which type of crop to be planted and also which type of fertilizer to use, the soil of the field to be planted must be analyzed.

In order to analyze the soil an individual normally would have to go into the field and by hand scoop up a number of soil samples which are mixed and later analyzed within a laboratory. As can be seen, when trying to take samples from a very large field it can be a very time consuming process. Certain devices have been developed which are mounted to a vehicle wherein whenever a soil sample is to be taken the vehicle is stopped and a probe is inserted into the soil which removes a small amount of the soil to be analyzed. These devices reduce the time which used to be spent taking a field soil sample however the vehicle still has to be stopped when the soil sample was taken.

There is a need for a soil sampler which may be mounted to a vehicle and more importantly is adapted to take soil samples while the vehicle is moving.

SUMMARY OF THE INVENTION

The present invention provides a soil sampling device which is easily mounted to a vehicle and has the important advantage of being able to take a series of soil samples and mix each separate soil sample together all while the vehicle is moving across the field.

The soil sampler is provided with an elongated generally rectangular shaped housing which has a first and second portion in open communication with each other. The second portion, or what is normally referred to as the lower portion, has a soil inlet opening in the front face thereof. The first portion, or what is generally referred to as the top or upper portion, has a chamber extending outwardly therefrom. A plurality of soil retaining baffles, which have the capability of being angularly adjustable, are disposed within the lower portion of the second portion adjacent the soil inlet opening. A large baffle extends from the first portion and across one end of the chamber. The housing is pivotally mounted to a mounting bar and brace, which is secured to the vehicle. A hydraulic piston is eccentrically connected to a first wheel and which is in communication with a second wheel, of a diameter less than the first wheel, which is then secured to the rod upon which the housing is pivotally mounted. The hydraulic piston is in communication with an activation device within the cab of the vehicle and also with the hydraulic system of the vehicle.

Whenever a soil sample is to be taken the hydraulic piston is retracted and the rotation of the wheels impart a very quick rotary movement to the housing. The second portion of the housing strikes the ground which injects soil into the opening and is retained by the baffles. Since the vehicle is moving while this operation is proceeding, the housing is kicked back by the movement of the vehicle over the ground, and this is absorbed by a spring connected to the piston. When the housing is returned to the inverted position by expansion of the piston the captured soil falls from the baffles into the upper portion of the first portion of the housing. When the housing is rotated to take a second sample this first captured soil is then directed into the chamber by a portion and the large baffle. With each successive soil sample additional captured soil is directed into the chamber through the rotary movement of the housing. When the soil sampler operation has been completed a door is opened on the end of the chamber and the total combined soil samples are extracted for analysis in a laboratory.

The present invention provides a simple, easy to operate continuous soil sampler which greatly reduces the time expended to take a field sample.

DETAILED DESCRIPTION OF THE PREFERRED EMBODIMENTS

Figure 2:
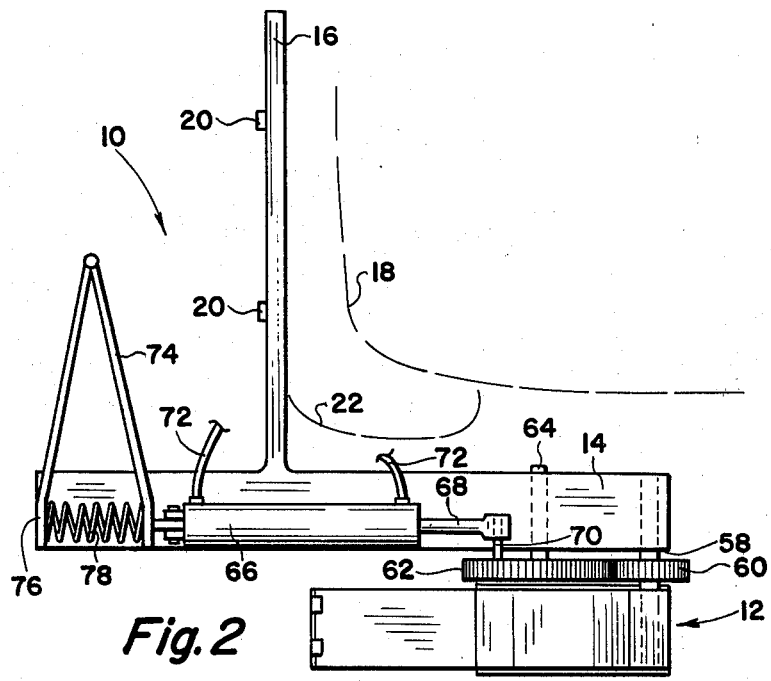
FIG. 2 is a top plan view of the device.
Figure 1:
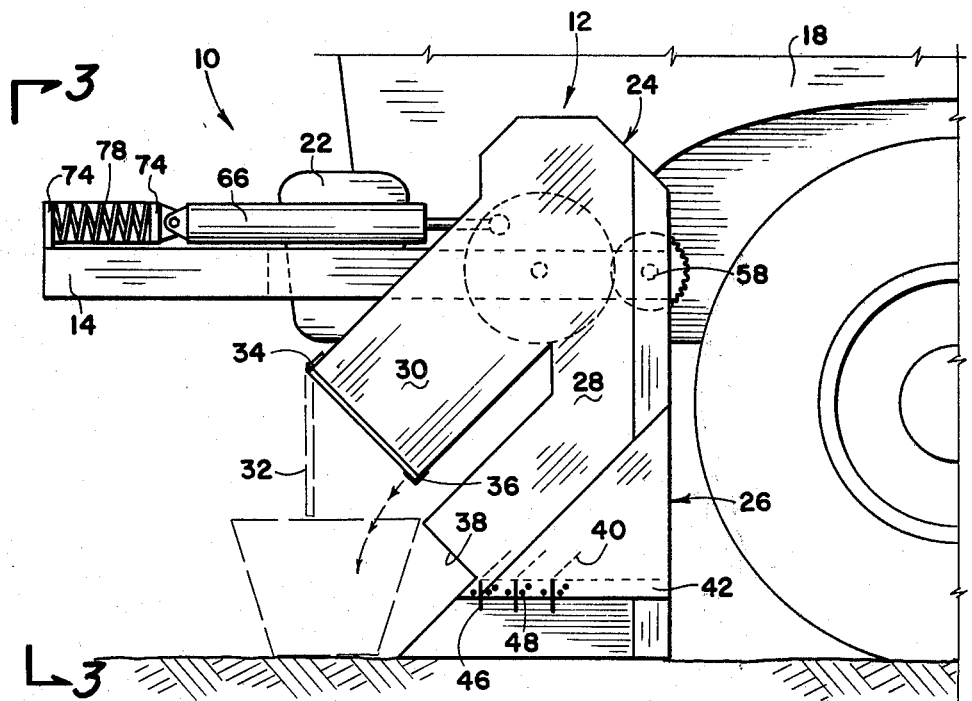
FIG. 1 is a side elevational view of a soil sampling device embodying the present invention connected to a vehicle.

Referring to the drawings in detail, reference character 10 generally indicates a soil sampling device which is mounted to a vehicle and is adapted to take any number of soil samples while the vehicle is moving. As shown in FIGS. 1 and 2, the soil sampling device 10 is generally comprised of a metal housing 12 which is pivotally mounted to a horizontal member or brace 14. The brace 14 is connected to a bar 16, which is connected to any suitable portion of a vehicle 18 by means of a plurality of bolts 20. The bar 16 is made of angle iron or the like and is preferably attached to a front bumper 22 of the vehicle 18.

The housing 12 is comprised of a first portion 24, a second portion 26 and a throat portion interconnected between the first and second portions 24 and 26 and in open communication with the other. An angled soil chamber 30 extends outward from and is in communication with the interior of the first portion 24. The chamber 30 is provided with an opening (not shown) at the extreme outer end thereof and is provided with a door 32 covering the opening. The door 32 is hingably connected to the chamber 30 by means of a plurality of hinges 34 and is maintained in a closed position thereover by a latch 36.

Figure 3:
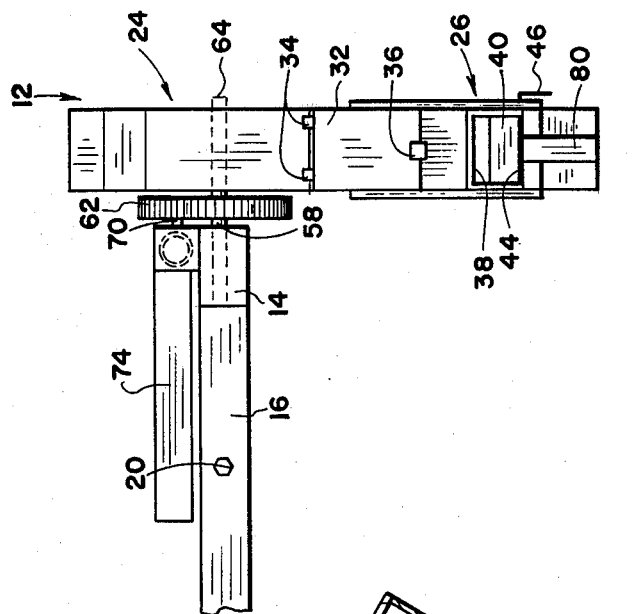
FIG. 3 is a view taken along line 3—3 of FIG. 1.

The second portion 26 of the housing 12 is provided with an opening 38, shown in FIG. 3, in the front portion thereof. Within the interior of the second portion 26, adjacent the opening 38, is a plurality of soil retaining baffle means 40 which are keyed to a flooring 42 in the second portion 26 by means of rods 44, which have angled handled portions 46 extending outwards and downwards from the flooring 42. The angle of the baffles 40 is rigidly maintained by means of a spring (not shown) biasing the handle portions 46 against and between a plurality of upstarts 46 on the outside surface of the flooring 42. The angle of each of the baffles 40 may be independently changed by means of rotating the handles 46 to a position between adjacent upstarts 48. This feature will be described in more detail herein below.

Figure 4:
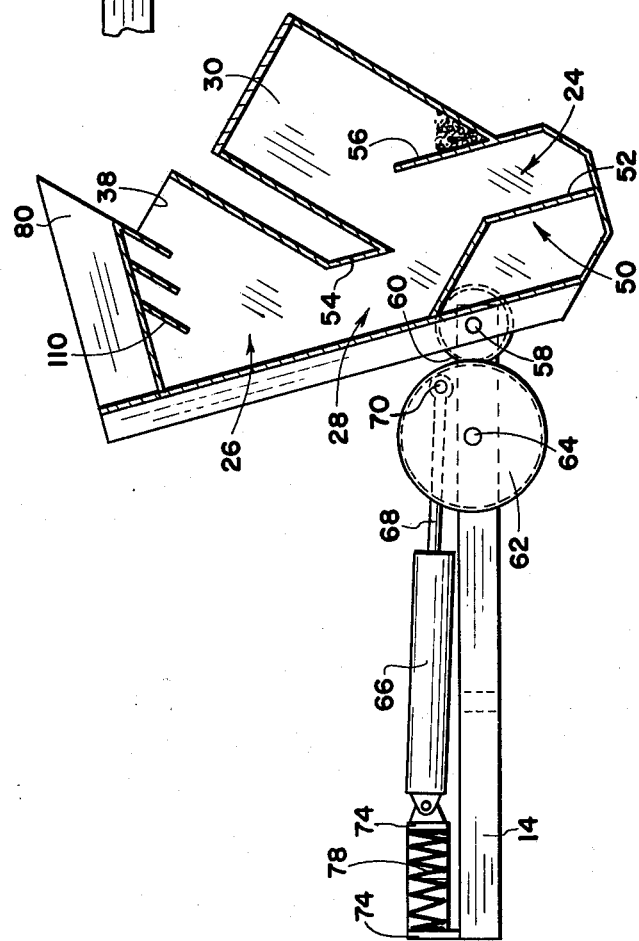
FIG. 4 is a side view of the device in the rest or traveling position.

As shown in FIG. 4, the interior of the first portion 24 is provided with a partition 50 which is spaced within the first portion 24 approximately opposite from the soil chamber 30. A side wall 52 of the partition 50 is spaced parallel with a side wall 54 of the throat portion 28 but is spaced out of line therewith towards the soil chamber 30. The soil chamber 30 is provided with a baffle 56 which extends partially into the soil chamber 30 from the first portion 24 and is parallel with the side walls 52 of the partition 50. The function of the partition 50 and the baffle 56 will be described in the operational description of the invention below.

The housing 12 is pivotally connected to the horizontal brace 14 by means of a rod 58, which passes through the housing 12 adjacent the first portion 24 and the partition 50. A wheel 60 is secured to the rod 58 and is in contact with a larger diameter wheel 62, which is in turn pivotally secured to the brace 14 by means of a rod 64. A hydraulic piston 66 is connected eccentrically to the larger diameter wheel 62 by means of a piston rod 68 and a pin 70 which passes from the piston rod 68 into the wheel 62. The hydraulic piston 68 is connected by means of a plurality of hoses 72 to the hydraulic system (not shown) of the vehicle 18. The end of the hydraulic piston 66 opposite from the piston rod 68 is connected to a hinge means 74 with one end thereof 76 rigidly secured to the horizontal brace 14. A spring 78 is spaced between the open members of the hinge 74. The hinge 74 acts to keep the spring 78 is axial alignment when the piston 66 is forced towards the spring. The spring 78 may be kept in alignment by being encapsulated within a cylinder (not shown) which would serve the same function as the hinge 74.

Figure 5:
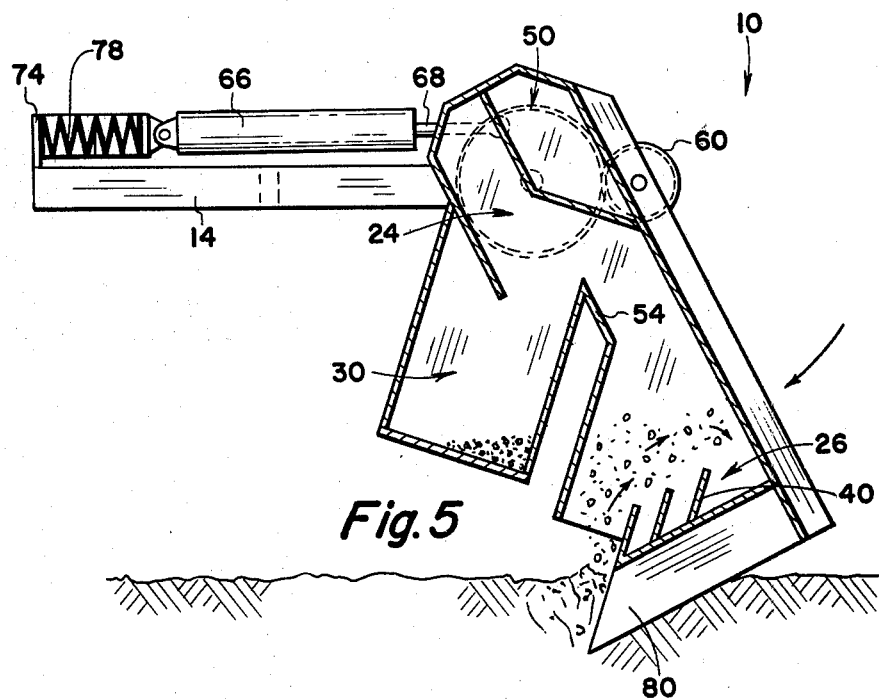
FIG. 5 is a side view of the device being rotated to strike the ground; to capture a soil sample.

To best understand the function of the soil sampling device 10 the sequential operation of the invention will be described below. FIG. 4 represents the rest position for the soil sampling device 10 when not in use and when the vehicle 18 is moving. When a soil sample is to be taken the operator applies hydraulic pressure to the piston 66 which quickly retracts the rod 68. As the rod 68 is withdrawn the larger diameter wheel 62 is rotated in the counterclockwise direction (as viewed in FIG. 4) which imparts a rapid clockwise rotation of increased velocity to the wheel 60 due to the difference in diameters. The housing 12 is thereby quickly rotated with a "whip-like" action which drives a bevelled shovel 80, which is attached to the flooring 42, into the ground as shown in FIG. 5. When the shovel 80 strikes the ground a small amount of soil is injected through the opening 38 into the second portion 26 and is captured between the plurality of baffles 40.

Figure 6:
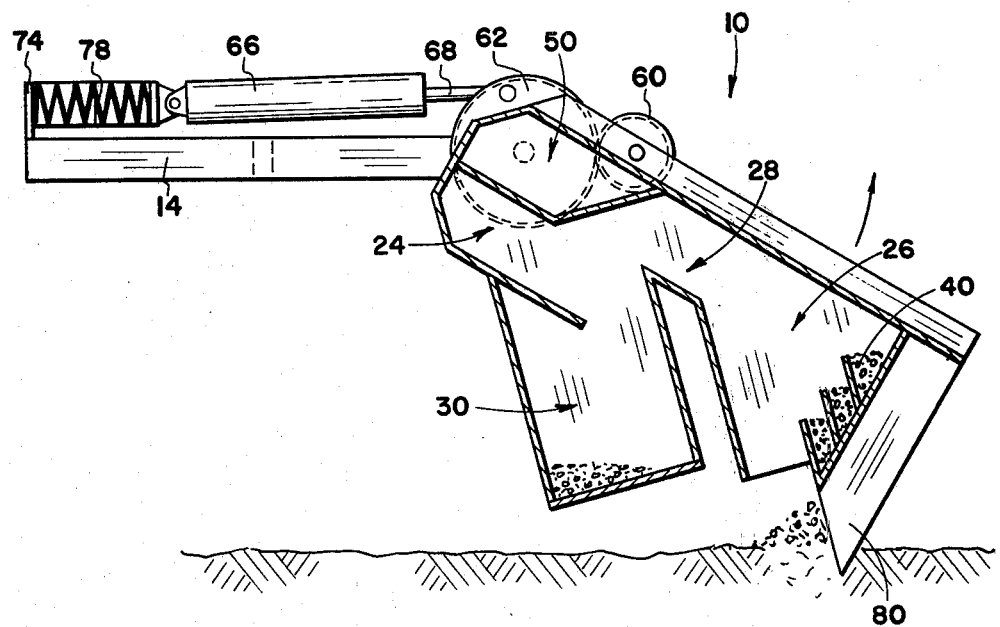
FIG. 6 is a side view of the device being rotated to the rest position.
Figure 7:
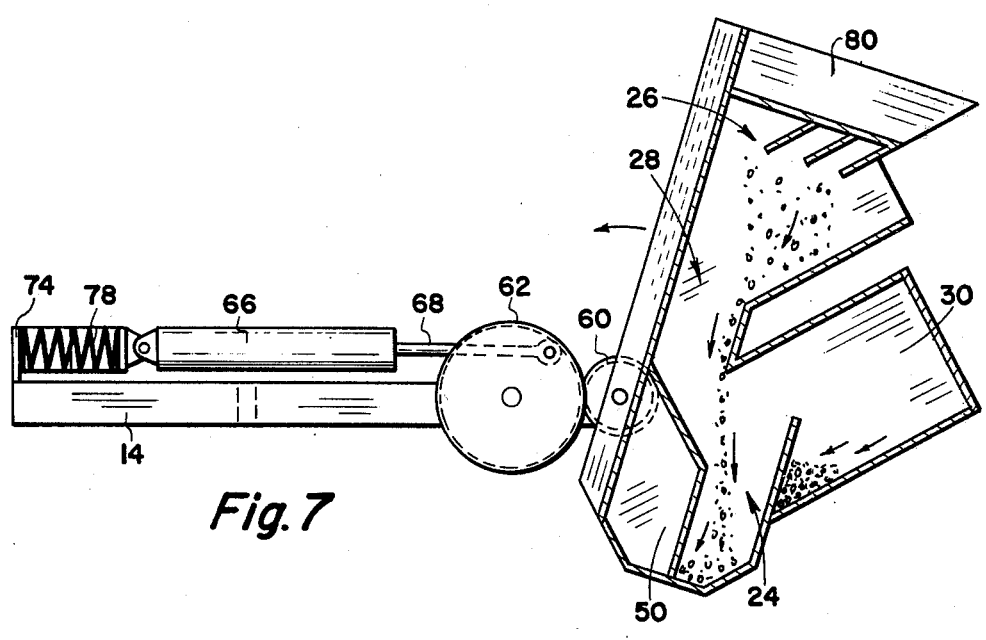
FIG. 7 is a side view of the device being rotated to the rest position and the soil sample falling into a first portion of the device.

Due to the forward movement of the vehicle 18 the housing 12 is "kicked back" in a counter-clockwise direction and the force of the intial impact in this is absorbed by the hinge 74 and the spring 78 as shown in FIG. 6. The operator then expands the piston 66 which will rotate the housing 12 in a counter-clockwise direction. As the housing 12 is brought into the inverted or rest position the soil that was captured between the plurality of baffles 40 falls by gravity as shown in FIG. 7, through the throat portion 28 and into the first portion 24 between the side wall 52 of the partition 50 and the baffles 56.

Figure 8:
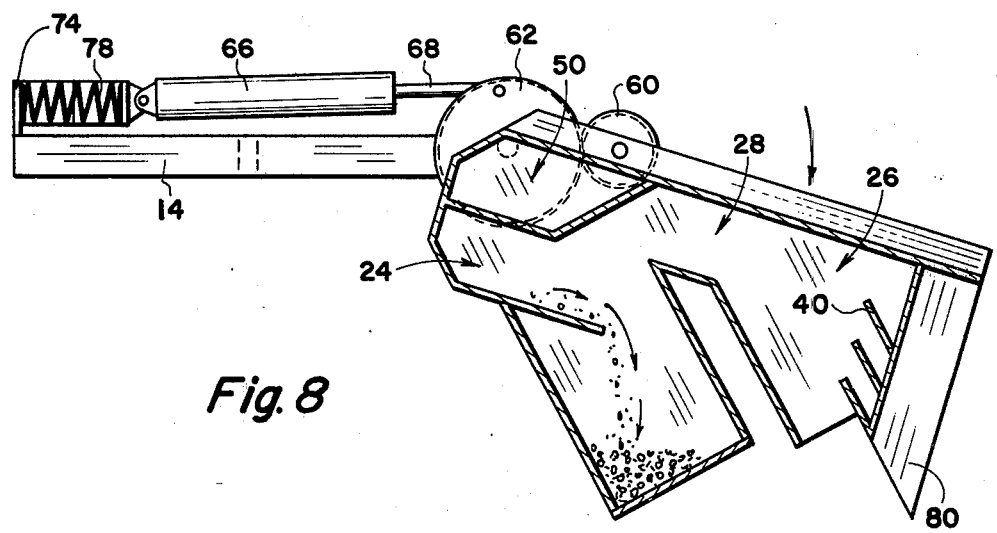
FIG. 8 is a side view of the device being rotated to strike the ground to take a successive soil sample and with the captured soil falling into a chamber in the device.

When the next soil sample is to be taken and the piston 66 is contracted to rotate the housing 12 into contact with the ground, the soil that was resting within the first portion 24 of the housing 12 falls into the soil chamber 30, as shown in FIG. 8. As can be seen with each successive cycle of taking a soil sample additional captured soil is transferred, simply by the rotation and the position of the internal features of the housing 12, from the baffles 40 into the soil chamber 30 and the soil is maintained therein by means of the baffle 56, as when the housing 12 is in the inverted or rest position as shown in FIG. 4. To adjust the amount of soil captured per cycle, the angle of the baffles 40 is adjusted as described above. This feature compensates for the texture and the moisture content of the soil which is to be sampled.

When the soil sampling has ceased and the accumulated captured soil is to be analyzed the housing 12 is rotated slowly so that the shovel 80 rest upon the ground, as shown in FIG. 1, and the door 32 is opened to allow the captured soil to be removed for analysis.

Whereas the present invention has been described in particular relation to the drawings attached hereto, it should be understood that other and further modifications of the invention, apart from those shown or suggested herein, may be made within the scope and spirit of this invention.

What is claimed is:

1. A soil sampling device secured to a vehicle for taking soil samples while the vehicle is moving, comprising:

a housing having a first and a second portions in open communication with each other, said second portion having a soil inlet means therein;

soil retaining means disposed within said second portion adjacent said soil inlet means;

a chamber extending outwardly from said first portion and in communication therewith;

baffle means interposed between said chamber and said first portion and extending across one end of said chamber;

mounting means attached to the vehicle; and means secured between said mounting means and said housing for selectively rotating said housing between an upright and an inverted positions, whereby when said housing is rotated to an upright position said second portion strikes the ground and soil inters said soil inlet means for capturing said soil.

2. A soil sampling device as in claim 1 wherein means provided within said first portion for directing said capturing soil into said chamber when said housing is rotated.

3. A soil sampling device as in claim 2 wherein said means for directing said captured soil being a partition spaced oppositely from said soil inlet means and said chamber within said second portion.

4. A soil sampling device as in claim 1 wherein said second portion being provided with soil piercing means adjacent said soil inlet means.

5. A soil sampling device as in claim 4 wherein said soil piercing means being a bevelled shovel adapted to pierce the soil and direct the soil into said soil inlet means.

6. A soil sampling device as in claim 1 wherein said retaining means confines said captured soil from when said soil enters said soil inlet means until said housing is rotated to an inverted position.

7. A soil sampling device as in claim 6 wherein said retaining means being adjustable to retain a selected amount of the captured soil.

8. A soil sampling device as in claim 6 wherein said soil retaining means being at least one baffle to selectively retain said captured soil.

9. A soil sampling device as in claim 8 wherein said baffle being provided with means to vary the angle thereof.

10. A soil sampling device as in claim 1 wherein said chamber and said baffle means being adapted to retain said captured soil in said chamber when the housing is rotated.

11. A soil sampling device as in claim 1 wherein said chamber being provided with an opening and door means across said opening, said door means being provided with latch means.

12. A soil sampling device as in claim 1 wherein said mounting means being a bar means attachable to said vehicle.

13. A soil sampling device as in claim 1 wherein said means for selectively rotating said housing comprising:
a brace connected to said mounting means;
means to pivotally connect said housing to said brace; and
means in communication with said housing to selectively impart rotary movement thereto.

14. A soil sampling device as in claim 13 wherein said means to selectively impart rotary movement to said housing comprises a hydraulic piston, said hydraulic piston being in communication with a first wheel, pivotally connected to said brace, and a second wheel, of a diameter less than said first wheel, secured to said means to pivotally connect said housing to said brace.

15. A soil sampling device as in claim 13 wherein shock absorbing means being in communication with said hydraulic piston.

* * * * *